US00RE35102E

United States Patent [19]

Zare et al.

[11] E Patent Number: Re. 35,102

[45] Reissued Date of Patent: Nov. 28, 1995

[54] CAPILLARY ELECTROPHORETIC DEVICE EMPLOYING STRUCTURE PERMITTING ELECTRICAL CONTACT THROUGH IONIC MOVEMENT

[75] Inventors: Richard N. Zare, Stanford; Xiaohua Huang, Mountain View; Raymond T. Huckaby, San Jose, all of Calif.

[73] Assignee: The Board of Trustees of the Leland Stanford Junior University, Stanford, Calif.

[21] Appl. No.: 149,024

[22] Filed: Nov. 8, 1993

Related U.S. Patent Documents

Reissue of:

[64] Patent No.: 4,908,116
Issued: Mar. 13, 1990
Appl. No.: 359,512
Filed: Jun. 1, 1989

U.S. Applications:

[63] Continuation of Ser. No. 849,101, Mar. 6, 1992, abandoned.

[51] Int. Cl.[6] ..... G01N 27/26; G01N 27/447

[52] U.S. Cl. ..... 204/180.1; 204/299 R

[58] Field of Search ..... 204/180.1, 299 R

[56] References Cited

U.S. PATENT DOCUMENTS

| | | | |
|---|---|---|---|
| 2,925,370 | 2/1960 | Rohrer | 204/435 |
| 3,282,818 | 11/1966 | Nolan | 204/295 X |
| 3,658,679 | 4/1972 | Stansell et al. | 204/409 |
| 3,697,406 | 10/1972 | Svendsen | 204/299 R |
| 3,948,753 | 4/1976 | Arlinger | 204/299 R |
| 4,729,947 | 3/1988 | Middendorf et al. | 204/182.8 |
| 4,908,116 | 3/1990 | Zare et al. | 204/299 R |

OTHER PUBLICATIONS

Donald J. Rose and James W. Jorgenson "Fraction Collector For Capillary Zone Electrophoresis" Journal of Chromatography 438 (1988) 23–34.

"Preparative Capillary Electrophoresis Based on Adsorption of the Solutes (Proteins) onto a Moving Blotting Membrane as They Migrate out of the Capillary," *Analytical Biochemistry*, 201:211–215 (1992).

Smith et al., "Improved Electrospray Ionization . . . ," *Anal. Chem.*, 60:1948–1952.

Wallingford et al., "Capillary Zone Electrophoresis with Electrochemical . . . ," *Anal. Chem.*, 59:1762–1766.

"Preparative Capillary Isotachophoresis Principle and Some Applications," by T. Arlinger, *Journ. of Chromatography*, vol. 119, Apr. 28, 1976.

"Capillary Zone Electrophoresis with Electrochemical Detection," Wallingford et al., *Analytical Chemistry*, vol. 59, No. 14, 15, pp. 1762–1766, Jul. 1987.

"On–Line Connector for Microcolumns: Application to the On–Column . . . ", by Pentoney et al., *Analytical Chem.*, vol. 60, No. 23, pp. 2625–2626, Dec. 1, 1988.

"On–Column Conductivity Detector for Capillary Zone Electrophoresis," by Huang et al., *Analytical Chem.*, vol. 59, (List continued on next page.)

*Primary Examiner*—John Niebling
*Assistant Examiner*—John S. Starsiak, Jr.
*Attorney, Agent, or Firm*—Majestic, Parsons, Siebert & Hsue

[57] ABSTRACT

A capillary tube has a structure in its wall that permits ions to flow but no substantial amount of electrolyte to move therethrough. The structure therefore permits electrical contact between the electrolyte inside the tube and the outside environment without diluting the electrolyte. The structure forms only a small part of the side wall so that the tube retains its structural integrity and can be used in electrophoresis without requiring structural support. In the preferred embodiment, the structure is formed by drilling a hole in the side wall, filling the hole with glass powder and fused silica and heating the mixture to form a frit structure to plug the hole. The frit structure permits ions to flow but substantially no electrolyte to move therethrough. Electrophoretic samples exiting from the end of the tube are not diluted and can be continuously collected, such as on top of a moving plate.

32 Claims, 4 Drawing Sheets

OTHER PUBLICATIONS

No. 23, pp. 2747–2749, Dec. 1, 1987.
"Capillary Electrophoresis," by Gordon et al., *Science,* vol. 242, pp. 224–228, Oct. 14, 1988.
"Use of an On–Column Frit in Capillary Zone Electrophoresis: Sample Collection," by Huang et al., *Analytical Chem.,* vol. 62, No. 5, Mar. 1990, pp. 443–336, Columbus, Ohio.
"Capillary Zone Electrophoresis with Fraction Collection for Desorption Mass Spectrometry," by Takigiku et al., *Analytical Abstracts Database,* Royal Society of Chemistry, Cambridge, GB, Abstract No. 52–10–J–0086, vol. 4, No. 1 pp. 24–29, Jan. 1, 1990.

Wallingford et al., "Amperometric Detection . . . ," *Anal. Chem.,* 60:258–263.

CAPILLARY ELECTROPHORETIC DEVICE EMPLOYING STRUCTURE PERMITTING ELECTRICAL CONTACT THROUGH IONIC MOVEMENT

Matter enclosed in heavy brackets [ ] appears in the original patent but forms no part of this reissue specification; matter printed in italics indicates the additions made by reissue.

*This is a continuation of application Ser. No. 849,101, filed Mar. 6, 1992, now abandoned, which is a reissue application of Ser. No. 07/359,512, filed Jun. 1, 1989, now U.S. Pat. No. 4,908,116.*

BACKGROUND OF THE INVENTION

This invention relates in general to capillary electrophoretic systems and in particular to an improved capillary tube with a structure that permits electrical contact through ionic movement and to a capillary electrophoretic system employing such a capillary tube.

Capillary zone electrophoresis (CZE) in small capillaries has proven useful in an efficient method for the separation of solutes. An electric field is applied between the two ends of a capillary tube into which an electrolyte containing the solutes is introduced. The electric field causes the electrolyte to flow through the tube. Some solutes will have higher electrokinetic mobilities than other solutes so that the sample components are resolved into zones in the capillary tube during the flow of the electrolytes through the capillary.

CZE is advantageous because it require only very small sample volumes, such as the contents of a cell or cellular subcompartments. For these and other reasons, CZE has shown great promise as a separation and detection technique.

A number of CZE detection schemes have been used. These schemes include optical detection based on optical properties of sample components. Other CZE detection schemes include conductivity detection and electrochemical detection. In conductivity detection, a conductivity detector detects the change in conductance between two points as different zones move through the detection region. In electrochemical detection, electroactive sample components are detected when they alter the voltage across or the current between two points near the detector.

In the electrophoresis process, a high voltage of the order of several tens of thousands of volts is applied between the two ends of a capillary tube in order to move the electrolyte and samples through the tube in a reasonable time and with reasonable resolution. Such high voltage used may create high electric fields at a detecting or measuring device which may introduce unacceptable noise or otherwise interfere with the measurement of such a device and which may, in the extreme, cause damage to the circuitry in the device. Therefore in order for conductivity or electrochemical detectors to function properly in an electrophoresis process, the electrolyte and sample at or near the location of detection should be either grounded or fixed at a low voltage which will not interfere with the measurements of the detectors.

In conductivity detection, the voltage across and current between two selected points are measured so that it is necessary to introduce two electrodes, one at each selected point. It is therefore desirable to provide electrophoretic devices that permit electrodes to be introduced at or near the points of detection or which otherwise provides means to at least maintain such points at ground or a low voltage.

In a conventional capillary electrophoresis system, each end of the capillary is dipped into a reservoir. A high voltage is then applied between the two reservoirs. Typically, a high voltage is applied to one reservoir and the other reservoir is grounded. The two reservoirs each contains an electrolyte buffer. Such a conventional system is described in "Capillary Electrophoresis" by Gordon, Huang, Pentoney, Jr. and Zare, reprint series from Science, Oct. 14, 1988, Vol. 242, pp. 224–228.

In the conventional capillary electrophoresis system, the reservoir connected to one of the two ends of the capillary is grounded so that conductivity and electrochemical detections may be performed near the tube at the location close to such reservoir. Such a conventional system is disadvantageous because any sample components collected will be diluted by the electrolyte buffer in the reservoir and the system does not permit continuous collection of sample components. Furthermore, since the detector itself in conductivity or electrochemical detection cannot be placed directly in the electrolyte buffer, but must be placed at a location at least a short distance removed from the reservoir, the sample components actually detected by the detector is not grounded or fixed at a set low voltage. This may result in serious inaccuracies in the measurements.

In view of the above disadvantages of the conventional electrophoresis system, various solutions have been proposed. One alternative electrophoresis system is disclosed in "Improved Electrospray Ionization Interface for Capillary Zone Electrophoresis-Mass Spectrometry" by Smith et al., Anal. Chem. 1988, 60, 1948–1952. In the paper, Smith et al. described a previous ionization interface where a metal electrode coated on the outlet of the capillary is used to ground the electrolyte and sample. As Smith et al. admitted in the paper, the process of depositing metal at a capillary terminus was time consuming and the deposited metal was slowly eroded by electrochemical processes and required replacement after several days of operation. In many cases, electrochemical reaction at the electrode lead to the evolution of gas bubbles which were extremely detrimental to the operation of the electrophoretic separation. This scheme also suffers from irreproducibility caused by electrochemical reaction at the grounding electrode.

In the same paper, Smith et al. also described another ionization interface utilizing a liquid sheath electrode. The actual CZE electrical contact is made to the low-voltage end of the capillary with a thin sheath of liquid that flows over the outside surface of the capillary. In such a scheme, the CZE effluent avoids contact with any metal surfaces and is isolated from loss by electrochemical reactions. The system is difficult to construct. With such a scheme, sample components collected will be diluted by the buffer liquid in the liquid sheath.

In "Capillary zone electrophoresis with electrochemical detection", Anal. Chem. 1987, 59, 1762–1766 and "Amperometric Detection of Catechols in Capillary Zone Electrophoresis with Normal and Micellar Solutions", Anal. Chem. 1988, 60, 258–263, Wallingford and Ewing disclosed a conductive joint made near the low-voltage end of the capillary by fracturing the capillary at such a point and encasing the fracture in a porous glass capillary whose inside diameter was large enough for encasing the sample holding capillary. The porous glass capillary permitted ionic movement through the fracture between the sample and an outside reservoir for grounding or for setting the electrolyte and sample at the fracture point to ground or a low voltage. Again this scheme is difficult to construct. Furthermore, the system had a dead volume (extra volume) at the fracture point which decreased sensitivity and resolution.

Because none of the above described schemes is entirely satisfactory, it is desirable to provide an electrophoretic device in which the above-described difficulties are alleviated.

SUMMARY OF THE INVENTION

One aspect of the invention is directed toward a capillary tube comprising a wall surrounding an axis. The wall defines a first space inside the wall and a second space outside the wall. The wall is suitable for containing and confining an electrolytic solution in the first space. The tube further comprises a structure in the wall extending between the first and second spaces. The structure does not completely surround the axis so that the wall retains its structural integrity and so that the tube is suitable for use in electrophoresis without requiring structural support. The structure permits ions but substantially no electrolytic solution to flow therethrough, so that said structure permits electrical contact between the first and second spaces through ionic movement.

Since the structure permits ionic movement between the first and second spaces, it is possible to ground or set the portion of the electrolyte and sample in the first space in the vicinity of the structure at ground or a low voltage. Hence, if the electrolyte and sample are introduced into the inlet end of the tube and a voltage is applied between the electrolyte and sample at the inlet end of the tube and those in the vicinity of the structure, the electrolyte and sample will flow from the inlet end towards the outlet end of the tube. Because the electrolyte and sample at or near the structure is set at ground or a low voltage, the electrolyte and sample downstream from the structure will also be at ground or a low voltage. Hence electrodes from conductivity or electrochemical detectors may be placed in the first space downstream from the structure for detecting the conductivity or electrochemical properties of the sample at ground or at low voltage.

Another aspect of the invention is directed toward a capillary electrophoretic device employing the tube described above and the means for applying an electrical potential between the electrolyte and sample at the inlet end of the tube and the electrolyte and sample at the structure.

Yet another aspect of the invention is directed toward a method for making a capillary tube with a frit structure for use in electrophoresis. The method comprises making a hole at one side of a capillary tube, inserting a body inside the tube to block the hole from a position inside the tube and filling at least a portion of the hole with a glass powder. A portion of the tube surrounding the hole and the glass powder is heated to a temperature at or near the sintering temperature of the glass powder so that the powder forms a frit structure. The body is then withdrawn from the tube.

Still another aspect of the invention is directed toward an electrophoretic method employing the capillary tube described above. An electrolyte and a sample are introduced into the tube. A voltage is applied between the sample and electrolyte at the inlet end of the tube and the sample and electrolyte at the structure so that the electrolyte and sample flow from the inlet end towards the outlet end. The effluent is then collected from the outlet end so that the sample component separated in the electrophoresis process can be isolated or collected.

DETAILED DESCRIPTION OF THE INVENTION

Figure 1:
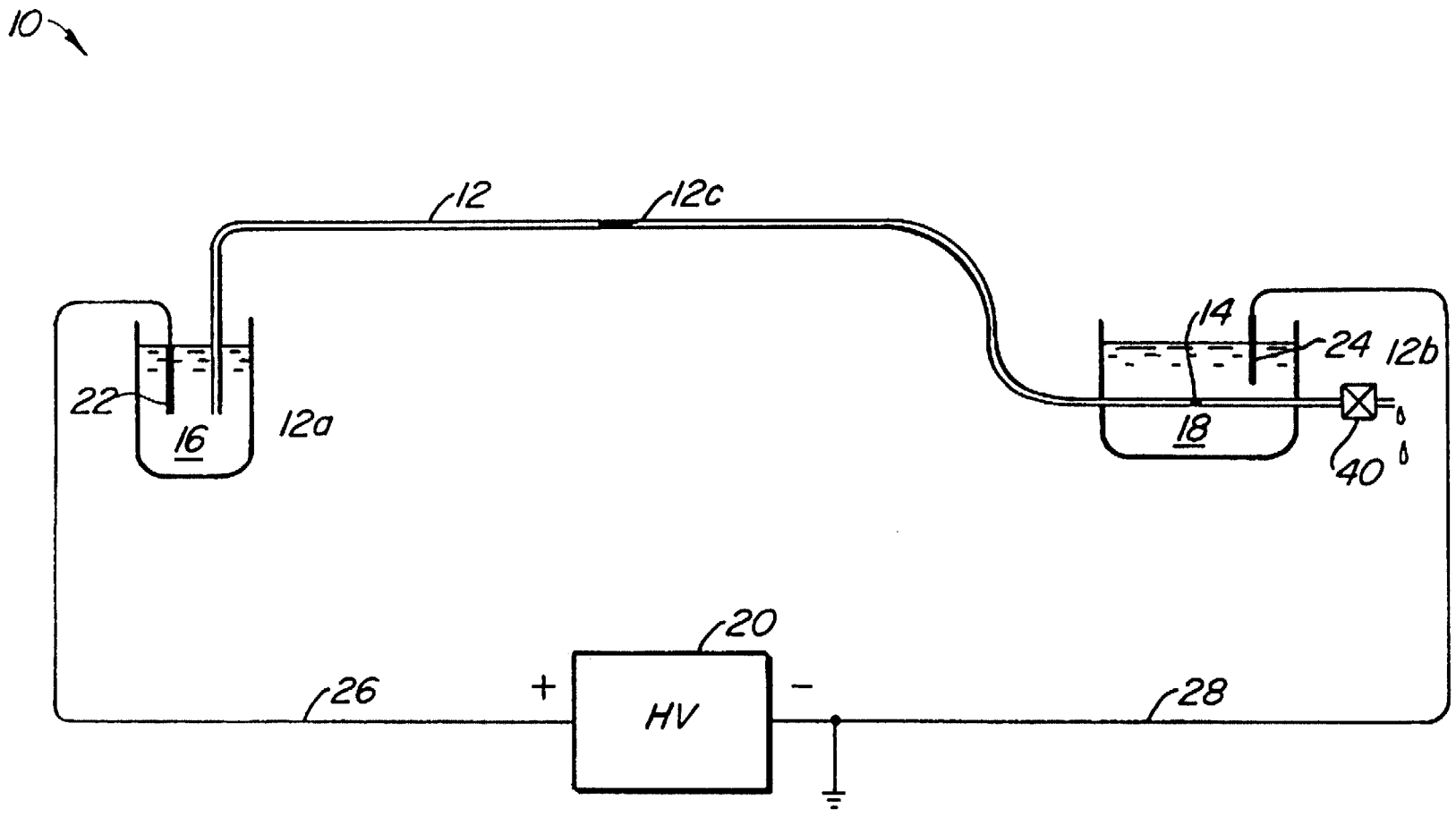
FIG. 1 is a schematic view of an electrophoretic system to illustrate the invention.

FIG. 1 is a schematic view of an electrophoretic system to illustrate the invention. The system 10 includes a capillary tube 12 with two ends 12a, 12b. Tube 12 defines a space 12c inside the tube that is separated from the outside environment by the tube. The tube has a structure 14 therein which permits the movement of ions therethrough between space 12c and the outside environment but substantially no flow of electrolyte or samples therethrough. End 12a is dipped in a reservoir 16 and structure 14 immersed in reservoir 18. A high voltage is applied to the electrolyte and sample introduced into space 12c by power source 20, electrodes 22, 24 and wires 26, 28, causing the electrolyte and sample introduced at end 12a to flow toward structure 14 and exit at end 12b. Since structure 14 permits movement of ions therethrough, the electrolyte and sample in space 12c in the vicinity of structure 14 will be at a potential substantially equal to that of reservoir 18.

In the preferred embodiment, wire 28 and electrode 24 are grounded so that the electrolyte and sample in space 12c in the vicinity of structure 14 is also substantially grounded. A high voltage is applied by source 20 through wire 26 and electrode 22 to reservoir 16. Therefore, a high potential difference exists between the electrolyte and sample at end 12a and those in space 12c in the vicinity of structure 14. Such potential difference causes the electrolyte and sample introduced into end 12c to flow toward structure 14 and exit at end 12b. Alternatively, instead of grounding reservoir 18 and structure 14, source 20 may apply a low voltage to reservoir 18. Such alternative arrangements are within the scope of the invention.

After the electrolyte and sample components pass structure 14 and move toward end 12b, they will remain at ground or other low voltage applied through electrode 24 until they exit at end 12b. Thus, detector 40 can be used to detect the sample at ground potential or a low voltage potential. System 10 therefore permits detector 40 to detect the sample at a low voltage or at ground so that conductivity and electrochemical detection can be accurately made by detector 40. The difficulties of other existing systems described above are thereby avoided.

System 10 avoids any detrimental effects resulting from electrochemical reaction at the grounding electrode and the evolution of gas bubbles. Furthermore, since structure 14 permits ionic movement but substantially no flow of sample or electrolyte therethrough, the electrolyte and sample components that exit at end 12b is not diluted by any buffer electrolyte or sheath liquid used in other existing systems. System 10 also permits continuous collection of samples so that the sample components separated by the electrophoretic process will remain separate and can be individually collected as separate components.

Figure 2:
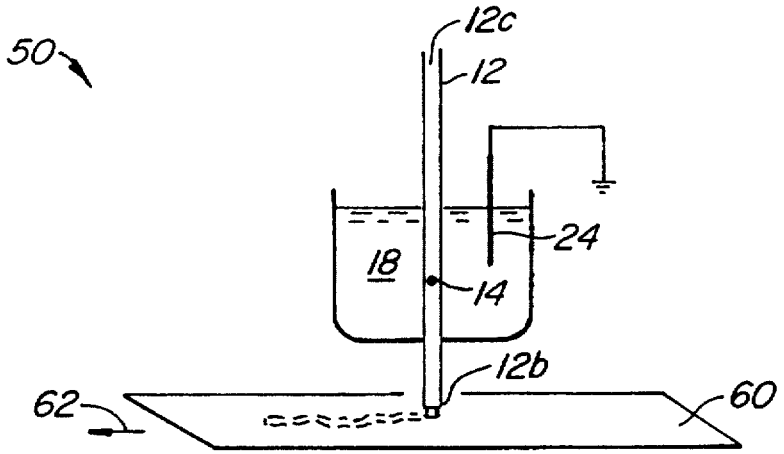
FIG. 2 is a schematic view of a portion of an electrophoretic system to illustrate another aspect of the invention.

FIG. 2 is a schematic view of a portion of an electrophoretic system 50 to illustrate another aspect of the invention. System 50 is similar to system 10 of FIG. 1 except that it includes in addition a surface 60, where surface 60 and end 12b move relative to each other. In FIG. 2, surface 60 is shown moving in direction 62 and end 12b is stationary. Alternatively, end 12b may be moved in a direction opposite to direction 62 and surface 60 kept stationary, or both surface 60 and end 12b are moved so that there is relative movement between them. These different implementations are within the scope of the invention. Identical components in the different figures of this application are numbered by the same numerals for simplicity.

As in system 10, a high voltage is applied between end 12a (not shown in FIG. 2) and structure 14, causing an electrolyte and samples introduced in end 12a to flow towards structure 14 and end 12b. As the electrolyte and sample components exit from end 12b, they are deposited onto surface 60 which is moving in direction 62. Hence the sample components that exit end 12b in a time sequence will remain as separate components deposited on the surface 60 in the same order in a spatial sequence. Such spatial sequencing of separated components of a sample permits easy analysis and detection in separation of the sample. Surface 60 may be moved at a constant speed or at adjustable speeds to improve the accuracy of separation and detection. Spatial sequencing and component separation can be achieved when end 12b is moved instead of surface 60, or when both are moved so that there is relative motion between them.

Structure 14 of FIGS. 1 and 2 may be made from a variety of materials. A frit structure made from a mixture of fused silica and glass powder is found to be satisfactory. One suitable type of glass powder that has been found to be satisfactory is Corning 7723.

Figure 3A:
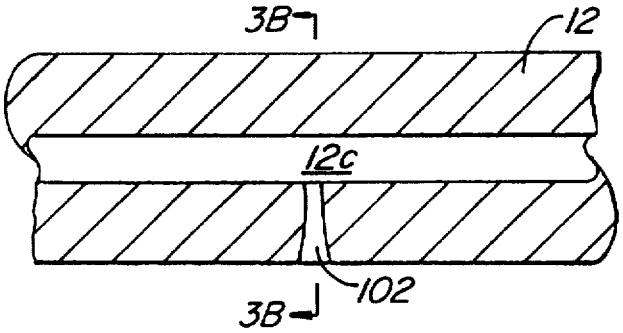
FIG. 3A is a cross-sectional view of a portion of a capillary tube with a hole in one side of the wall to illustrate the invention.

The method of creating structure 14, such as a frit structure, is illustrated in reference to FIGS. 3A, 3B, 4–6, 7A and 7B. In each of these figures, only a portion of capillary tube 12 including the structure is shown. As shown in FIG. 3A, a hole 102 is made in one side of tube 12. The hole may be made in a number of ways. The methods for making a hole in the side of a capillary tube are discussed in two related U.S. patent applications, "Capillary Device", Ser. No. 235,953, filed Aug. 24, 1988, and "On-column Conductivity Detector for Microcolumn Electrokinetic Separations", Ser. No. 63,547, filed Jun. 17, 1987. As disclosed in the later application, access holes may be made in the side of a capillary tube by a laser drill, ion beam drill, electroerosion, chemical etching (e.g. HF etching of glass or other inorganic silicious columns or chemical etching of organic columns), where the size of the hole is suitable for accepting an electrode as well as minimal but adequate amounts of adhesive/sealant. The specifications of the above two referenced patent applications are incorporated herein by reference to show different methods of making holes in capillary tubes and the inserting and sealing of "on-column" electrodes.

Figure 3B:
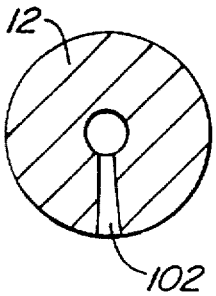
FIG. 3B is a cross-sectional view of the portion of FIG. 3A along the lines 3B–3B in FIG. 3A.

In the preferred embodiment, the hole can be made by directing a laser beam toward one side of tube 12. A carbon dioxide laser operating at about 20 watts has been found to give satisfactory results. A laser pulse of about 500 microseconds is directed toward one side of tube 12, and a hole 102 with dimensions varying from about 20 to 40 microns in diameter was made in the side of a capillary tube which is about 75 microns in diameter. Obviously, other types of lasers operating at other power levels may be used to direct different kind of pulses for the same purpose. All such variations are within the scope of the invention. FIG. 3B is a cross-sectional view taken along the lines 3B—3B of FIG. 3A to illustrate hole 102.

Figure 4:
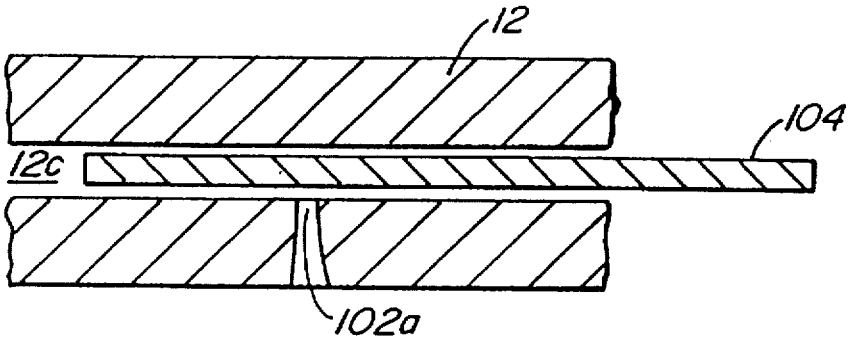
FIG. 4 is a cross-sectional view of the portion of FIG. 2 with a metal wire therein to illustrate the invention.

After hole 102 has been made, a metal wire is inserted in space 12c. This is illustrated in FIG. 4. Wire 104 blocks end 102a of the hole.

Figure 5:
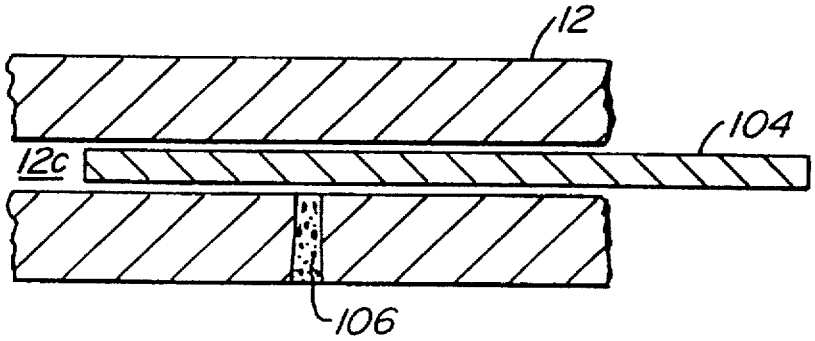
FIG. 5 is the cross-sectional view of the tube portion and wire of FIG. 3 where the hole is filled with a glass powder to illustrate the invention.

FIG. 5 is the cross-sectional view of the tube portion and wire of FIG. 4, where hole 102 has been filled by a mixture 106 of fused silica and glass powder. Since end 102a of the hole 102 has been blocked by wire 104, this prevents the fused silica and glass powder mixture from entering space 12c. If the mixture is allowed to enter space 12c, the mixture may create obstructions in space 12c or totally block the flow of any fluids through space 12c.

Figure 6:
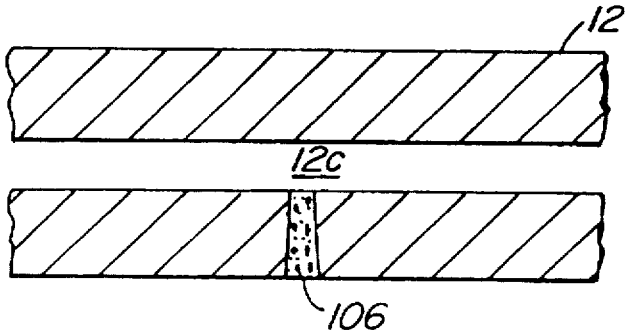
FIG. 6 is the cross-sectional view of the tube portion of FIG. 5 where the hole is filled with the glass powder, but before the tube is heated to sinter the glass powder.
Figure 7A:
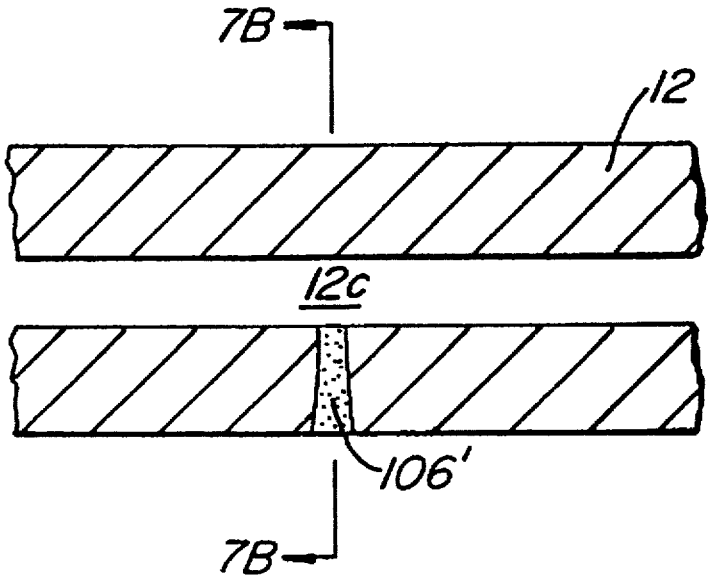
FIG. 7A is the cross-sectional view of the tube portion of FIG. 6 after the tube has been heated to a temperature to create a frit structure in the hole.
Figure 7B:
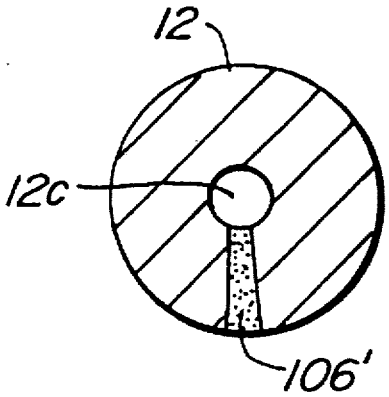
FIG. 7B is a cross-sectional view taken along the lines 7B–7B in FIG. 7A.

FIG. 6 is a cross-sectional view of the tube portion of FIG. 5 but after wire 104 has been withdrawn. The portion of tube 12 containing mixture 106 is then heated by a conventional method (such as in an oven) to a temperature just below the sintering temperature. This causes the fused silica and the glass powder to melt. When the mixture 106 is cooled, a frit structure 106' is formed as shown in FIG. 7A, where the frit structure permits ionic movement therethrough but substantially no flow of electrolyte or samples between space 12c and the outside environment. Therefore, frit structure 106' permits electrical contact through ionic movement but still confines the electrolyte and sample within space 12c without dilution.

The composition of the frit mixture can vary considerably and still achieve the desired results. Thus, the proportion of Corning Solder Glass 7723 may vary from 50% to 90% by volume and the proportion of fused silica may vary from 50% to 10% by volume. The fused silica can also vary in size from 1 to 10 microns in diameter. The sintering temperature of solder glass is about 770° C. and that of fused silica is about 2000° C. It has been found that satisfactory frit structures can be made by heating the mixture to about 1000° C. for about 30 seconds. As indicated above, structure 14 may be constructed in a manner different from that of frit structure 106' described above and can also be constructed using different materials such as asbestos, ceramic or metal oxide powders; such alternative constructions of structure 14 are within the scope of the invention.

From the above description, it is seen that the structure 14 or 106' in hole 102 can be made to form only a small portion of one side of the capillary tube. The structure does not surround the axis of the capillary tube or space 12c. Hence the incorporation of the structure does not significantly affect the structural integrity of the capillary tube so that the tube can still be used in electrophoretic processes without any structural support. Furthermore, since hole 102 can be completely filled, the above described structure can be made so that there is substantially no dead volume created thereby. This is in contrast to the above-described conductive joint device of Wallingford and Ewing which contains a considerable dead volume at the fracture point. This feature of the invention increases sensitivity and resolution of the electrophoretic detection and separation.

The above described method of making structure 106' is simple and reproducible. An electrophoretic device employing a capillary tube with a structure such as that described above can be used for electrophoretic detection and separation in a predictable and reproducible manner. The sample components are not diluted and the system permits continuous collection of sample components whereby the separated components remain separate.

While the invention has been described with reference to particular ingredients, methods and structures, it will be understood that modifications may be made without varying from the scope of the invention as defined by the appended claims.

What is claimed is:

1. A capillary tube *having an inlet hole and an outlet hole,* comprising:

a wall [surrounding an axis] *extending between the inlet hole and the outlet hole*, said wall defining a first space inside the wall and a second space outside the wall, said wall suitable for containing and confining an [electrolytic solution] *electrolyte* in the first space, *said outlet hole permitting a solution to flow through it*; and

[a] *at least one frit* structure in the wall extending between the first and second spaces [said structure not completely surrounding the axis so that the wall retains its structural integrity and so that the tube is suitable for use in electrophoresis without requiring structural support,] *and between the inlet and the outlet holes*, wherein said structure permits ions *to pass* but substantially no [electrolytic] solution to flow therethrough, so that said structure permits electrical contact between the first and second spaces through ionic movement.

[2. The tube of claim 1, wherein said structure is a frit structure.]

3. The tube of claim [2] *1*, wherein the *at least one* frit structure is created by making a hole in one side of the tube, inserting an object into the first space to block one end of the hole, filling at least a portion of the hole with a glass powder and heating the powder at a temperature close to the sintering temperature of the glass powder.

4. The tube of claim [2] *1*, wherein said *at least one* frit structure is composed of fused silica and solder glass.

5. A capillary electrophoretic device comprising:

a tube having an inlet and an outlet [end], *said tube being unbranched between the inlet and the outlet,* said tube including:

(a) a wall [surrounding an axis, said wall] defining a first space inside the wall and a second space outside the wall, said wall suitable for containing and confining an [electrolytic solution] *electrolyte* and electrophoretic sample in the first space;

(b) a structure in the wall extending between the first and second spaces, [said structure not completely surrounding the axis so that the wall retains its structural integrity and so that the tube is suitable for use in electrophoresis without requiring structural support,] wherein said structure permits ions *to pass* but substantially no [electrolytic] solution to flow therethrough, so that said structure permits electrical contact between the first and second spaces through ionic movement; and means for applying an electrical potential [between] *across* the electrolyte and sample [at] *between* the inlet [end] of the tube and the [electrolyte and the sample at the] structure *so that the inlet and the structure are at different electrical potentials, said structure located between the inlet and the outlet of the tube so that the electrical potential applied by the applying means causes the sample in the first space to flow out of the outlet.*

6. The device of claim 5, said electrical potential applying means comprising a first reservoir in contact with said inlet [end] of the tube and a second reservoir in contact with the structure, said first and second reservoirs being at different electrical potentials.

7. The device of claim 5, *wherein said electrolyte is a solution, and* wherein the electrical potential applied by the applying means causes [an] *the* electrolyte in the first space to flow from the inlet [end] toward the outlet [end], said device further comprising a detector placed adjacent to or inside the tube at a point between the structure and the outlet [end] for detecting the electrolyte at an electrical potential substantially equal to the electrical potential of the structure.

8. The device of claim 5, *wherein said electrolyte is a solution, and* wherein the electrical potential applied by the applying means causes [an] *the* electrolyte in the first space to flow from the inlet [end] towards the outlet [end], said device further comprising means for collecting samples of the electrolyte that flows from the tube at the outlet [end].

9. The device of claim 5, wherein said structure is a frit structure.

10. The tube of claim 9, wherein said frit structure is composed of fused silica and solder glass.

[11. A method of making a capillary tube with a frit structure for use in electrophoresis comprising:

making a hole at one side of a capillary tube;

inserting a body inside the tube to block the hole from a position inside the tube;

filling at least a portion of the hole with glass powder;

heating a portion of the tube surrounding the hole and the glass powder to a temperature at or near the sintering temperature of the glass powder so that the powder forms the frit structure; and withdrawing the body from the tube.]

[12. The method of claim 11, wherein the making step comprises directing a laser beam at said one side of the capillary tube.]

13. An electrophoretic method employing a capillary tube having [a first] *an inlet* and [a] *an* outlet [end], *said tube being unbranched between the inlet and the outlet,* said tube including: (i) a wall [surrounding an axis, said wall] defining a first space inside the wall and a second space outside the wall, said wall suitable for containing and confining an [electrolytic solution] *electrolyte* in the first space; (ii) a structure in the wall extending between the first and second spaces [said structure not completely surrounding the axis so that the wall retains its structural integrity and so that the tube is suitable for use in electrophoresis without requiring structural support,] *and located between the inlet and the outlet*, wherein said structure permits ions *to pass* but substantially no [electrolytic] solution to flow therethrough, so that said structure permits electrical contact between the first and second spaces through ionic movement; said method comprising:

introducing an electrolyte and a sample into the tube;

applying a voltage across the sample and electrolyte [at] *between* the inlet [end] of the tube and the [electrolyte and sample at the] structure so that the [electrolyte and sample flow from the inlet end toward the outlet end] *inlet and the structure are at different electrical poten-*

*tials, thereby causing the sample to separate into its components and flow out from the outlet*; and collecting the effluent from the outlet [end] so that the sample components separated in the electrophoresis process remain separate.

14. The method of claim 13, wherein the collecting step causes relative motion between the outlet [end] and a surface and deposits the effluent onto the surface in order to record the effluent output as a function of time.

15. The method of claim 14, wherein the collecting step moves the surface.

16. The method of claim 14, wherein the collecting steps moves the outlet [end].

*17. A method for electrophoretic separation comprising the steps of:*

*providing a capillary tube having an inlet and an exit, said capillary having no side branch between the inlet and the exit, said capillary containing a sample and electrolyte;*

*applying an electrical potential across the electrolyte and sample in a section of the capillary tube to cause electrophoretic separation of the sample into its components; wherein the electrical potential applied causes the separated components to flow out of the exit of the capillary tube; and*

*collecting and maintaining said separated components in a separated state.*

*18. A method as in claim 17 wherein the collecting and maintaining step comprises the steps of:*

*positioning a collection device in flow communication with the exit of the capillary tube; and*

*distributing the separated components spatially on the collection device.*

*19. A method as in claim 18 wherein the distributing step comprises the step of causing relative motion between a collection device and the exit of the capillary tube such that the separated components are spatially distributed and remain separated.*

*20. A method as in claim 19 wherein the collection device is a continuous surface.*

*21. A method as in claim 20 wherein the step of applying electrical potential comprises the step of providing at least one structure along the capillary tube near the exit, wherein said structure allows ionic contact with the electrolyte from outside the tube.*

*22. A method as in claim 21 further comprising the step of providing a detector for detecting the presence of the separated components migrating in the capillary tube.*

*23. A method as in claim 22 wherein the detector is provided at a location between the structure and the exit of the capillary tube.*

*24. A system for electrophoretic separation comprising:*

*a capillary tube having an inlet and an exit, said capillary tube having no side branch between the inlet and exit, the capillary containing a sample and electrolyte;*

*means for applying an electric potential across the electrolyte and sample in a section of the capillary tube to cause electrophoretic separation of the sample into its components;*

*means for causing the separated components to flow out of the exit of the capillary tube; and*

*means for collecting and maintaining said separated components in a separated state.*

*25. A system as in claim 24 wherein the collecting and maintaining means comprises:*

*a collection means positioned in flow communication with the exit of the capillary tube; and*

*means for distributing the separated components spatially on the collection means.*

*26. A system as in claim 25 wherein the means for distributing causes relative motion between the collection means and the exit of the capillary tube such that the separated components are distributed and remain separated.*

*27. A system as in claim 26 wherein the collection means is a continuous surface.*

*28. A system as in claim 27 wherein the applying means comprises at least one structure along the capillary tube near the exit which allows ionic contact with the electrolyte from outside the tube.*

*29. A system as in claim 28 wherein the causing means applies an electric potential across the section of the capillary tube.*

*30. A system as in claim 29 further comprising a detector for detecting the presence of the separated components in the capillary tube.*

*31. A system as in claim 30 wherein the detector is positioned at a location between the structure and the exit of the capillary tube.*

*32. The device of claim 5, wherein the electrical potential applied by the applying means causes the electrolyte and sample in the first space to flow from the inlet toward the outlet, said device further comprising a detector placed adjacent to or inside the tube at a point between the structure and the outlet for detecting the sample at an electrical potential substantially equal to the electrical potential of the structure.*

*33. The device of claim 5, wherein said wall surrounds an axis, said structure not completely surrounding the axis so that the wall retains its structural integrity and so that the tube is suitable for use in electrophoresis without requiring structural support.*

*34. The device of claim 5, wherein the electrical potential applied by the applying means causes the electrolyte and sample in the first space to flow from the inlet towards the outlet, said device further comprising a collector device collecting the sample that flows from the tube at the outlet.*

*35. The capillary tube of claim 1, wherein said first space has cross sectional dimensions of the order of 75 microns.*

* * * * *